United States Patent [19]

Martel et al.

[11] Patent Number: 4,463,014

[45] Date of Patent: Jul. 31, 1984

[54] CYCLOPROPANE CARBOXYLATES

[75] Inventors: Jacques Martel, Bondy; Jean Tessier, Vincennes; Jean-Pierre Demoute, Montreuil sous Bois, all of France

[73] Assignee: Roussel Uclaf, Paris, France

[21] Appl. No.: 365,462

[22] Filed: Apr. 5, 1982

[30] Foreign Application Priority Data

Apr. 16, 1981 [FR] France ............................. 81 07660

[51] Int. Cl.³ ...................... A01N 53/00; C07C 69/74; C07C 69/743; C07C 69/747
[52] U.S. Cl. ............................... 424/275; 260/465 D; 424/274; 424/279; 424/304; 424/305; 424/306; 424/308; 548/551; 549/66; 549/475; 560/65; 560/73; 560/105; 560/118; 560/124
[58] Field of Search ............... 260/465 D; 560/55, 65, 560/73, 105, 118, 124; 542/429; 424/274, 275, 279, 304, 308, 305, 306

[56] References Cited

U.S. PATENT DOCUMENTS

| | | | |
|---|---|---|---|
| 3,666,789 | 5/1972 | Itaya et al. | 560/124 |
| 4,199,596 | 4/1980 | Fuchs et al. | 560/124 X |
| 4,299,839 | 11/1981 | Omura et al. | 560/124 X |
| 4,318,922 | 3/1982 | Fuchs et al. | 560/124 X |
| 4,331,682 | 5/1982 | Ackermann et al. | 560/124 X |
| 4,376,786 | 3/1983 | Maurer et al. | 560/124 X |

*Primary Examiner*—Richard Raymond
*Attorney, Agent, or Firm*—Charles A. Muserlian

[57] ABSTRACT

Esters in their stereoisomeric form or mixtures thereof of the formula

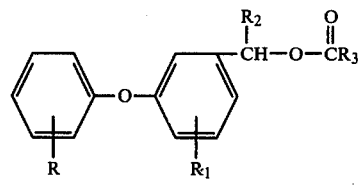

wherein $R_1$ and $R$ are different and individually selected from the group consisting of hydrogen, fluorine and bromine, $R_2$ is selected from the group consisting of —CN and —C≡CH and $R_3$ is a hydrocarbyl group having pesticidal properties and their preparations.

28 Claims, No Drawings

CYCLOPROPANE CARBOXYLATES

STATE OF THE ART

Belgium Pat. No. 853,411 describes phenoxy benzyl esters of the alcohol moiety of formula I with different acid moieties having insecticidal and acaricidal activity.

OBJECTS OF THE INVENTION

It is an object of the invention to provide the novel esters of formula I and a process for their preparation.

It is another object of the invention to provide novel pesticidal compositions and a novel method of combatting pests.

These and other objects and advantages of the invention will become obvious from the following detailed description.

THE INVENTION

The novel compounds of the invention are esters in their stereoisomeric form or mixtures thereof of the formula

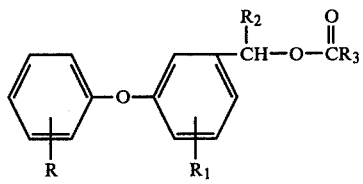

wherein $R_1$ and R are different and individually selected from the group consisting of hydrogen, fluorine and bromine, $R_2$ is selected from the group consisting of —CN and —C≡CH and $R_3$ is selected from the group consisting of

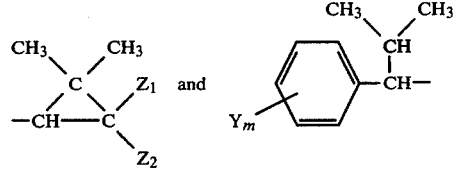

$Z_1$ and $Z_2$ are methyl or $Z_1$ is hydrogen and $Z_2$ is selected from the group consisting of

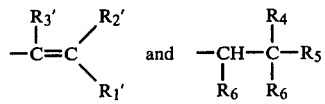

$R_3'$ is selected from the group consisting of hydrogen and halogen, $R_1'$ and $R_2'$ are individually selected from the group consisting of fluorine and alkyl of 1 to 8 carbon atoms or taken together with the carbon atom to which they are attached form cycloalkyl of 3 to 6 carbon atoms or

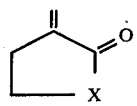

and X is selected from the group consisting of —O—, —S— and —NH—, $R_4$, $R_5$ and $R_6$ are individually halogen, Y may be in any ring position and is selected from the group consisting of halogen, alkyl of 1 to 8 carbon atoms, alkoxy of 1 to 8 carbon atoms and

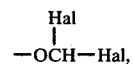

Hal is halogen and m is 0, 1 or 2.

Examples of $R_3'$ are hydrogen and halogen such as fluorine, bromine and chlorine. Examples of $R_1'$ and $R_2'$ are methyl, ethyl, n-propyl, isopropyl and branched or linear butyl, pentyl, hexyl, heptyl and octyl or together with the carbon atom form cyclopropyl, cyclobutyl, cyclopentyl or cyclohexyl.

Examples of $R_4$, $R_5$ and $R_6$ are halogens such as fluorine, chlorine or bromine and Hal is preferably fluorine. Examples of Y are halogens such as fluorine, chlorine or bromine, alkyl such as methyl, ethyl, isopropyl, n-propyl and branched and linear butyl, pentyl, hexyl, heptyl and octyl, alkoxy such as methoxy, ethoxy, propoxy, isopropoxy, branched and linear butoxy, pentyloxy, hexyloxy, heptyloxy and octyloxy and difluoromethoxy.

Among the preferred compounds of formula I are those wherein $R_2$ is —CN, those wherein R is hydrogen, those wherein $R_1$ is fluorine, especially in the 4-position, those wherein $R_3$ is

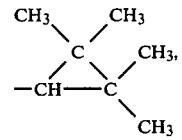

those wherein $R_3$ is

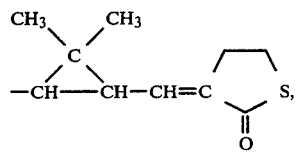

those wherein $R_3$ is

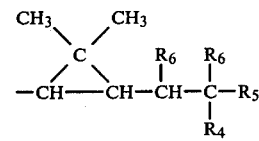

and $R_4$, $R_5$ and $R_6$ are halogen and those wherein $R_3$ is

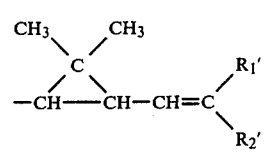

and $R_1'$ and $R_2'$ are with the carbon atom cycloalkyl of 3 to 6 carbon atoms.

The novel process of the invention for the preparation of compounds of formula I comprises reacting an acid of the formula $R_3$—COOH II wherein $R_3$ has the above definition or a functional derivative thereof with a racemic or optionally active alcohol of the formula

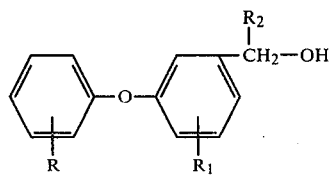

wherein R, $R_1$ and $R_2$ have the above definitions and optionally separating the desired stereoisomer by a physical or chemical means. Examples of physical means are chromatography or fractional crystallization.

In a preferred mode of the process, the functional derivative of the acid is the acid chloride but other known methods may be used to prepare the cyclopropane carboxylic acid esters such as reacting the acid and alcohol in the presence of dicyclohexylcarbodiimide.

The products of formula II are described in French Pat. Nos. 2,185,612, 2,364,884, 2,045,177 and 2,097,244. The racemic alcohols of formula III are described in French application Ser. No. 2,351,096 and the preparation of an optically active isomer of the alcohols of formula III is described in the examples.

The pesticidal compositions of the invention are comprised of a pesticidally effective amount of at least one compound of formula I and an inert carrier. The compositions are useful for combatting vegetable parasites, parasites of premises and parasites of warm-blooded animals. They are useful for combatting insects, nematodes, vegetable acariens warm-blooded animal acariens, and acariens of premises.

The compositions of the invention are especially useful as insecticides against insects in the agricultural field and are useful against ticks, lepidoptera and coleoptera larvae, for instance. They are usually used at a dose of 10 to 300 g of active ingredient per hectare. In addition the compositions have a good insecticidal activity against premises insects such as flies, mosquitoes and beetles.

The compositions destined for agrochemical use and use in premises may contain more than one active agent and may also contain other pesticides. The said compositions may be in the form of powders, granules, suspensions, emulsions, solutions, aerosol solutions, combustible strips, baits or other classical preparations used for compositions of this nature.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I.

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight, preferably.

In the case of a serpentine insecticide, the inert support may be made, for example, of pyrethrum stalks, Tabu powder (or Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for use in premises may be prepared as a spraying oil containing the active ingredient and the oil may soak the wick of a lamp which is then subjected to combustion. The concentration of the compound of formula I in the oil is preferably 0.03 to 95% by weight of the active ingredient.

The pesticidal compositions of the invention are also useful for combatting animal and vegetable acariens such as Tetranychus Urticae and parasitic nematodes such as Panagrellus Silusiae.

The acaricidal and nematocidal compositions of the invention may also contain one or more other pesticides and are in the usual powder, granule, suspension, emulsion or solution form. For vegetable acaricide use, the compositions are preferably wettable powders for foliar spraying containing 1 to 80% of the active ingredient or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

The pesticidal compositions of the invention are also useful for combatting animal parasites such as ticks and especially ticks of the Boophilus species, of the Hyalomnia species, of the Amblyomnia species and the Rhipicephalus species and for combatting all sorts of scabies, especially sarcoptic scabies, psoroptic and chorioptic scabies.

The compositions of the invention show an excellent general tolerance and are equally useful as medicaments for treating affections created by ticks and scabies. The compositions may be used in veterinary and human medicines. In human medicine, the compositions may be used to combat lice as well as prevent or treat scabies. The compositions may also be used as anthelmintics.

The said medicaments may be administered externally by vaporization, by painting or by bathing. For veterinary usage, the compositions may also be administered by painting the dorsal spine by the "pour on" method as well as being administered digestively or parenterally.

The pharmaceutical compositions of the invention contain at least one compound of formula I as the active ingredient and when they are destined to be used against acarien parasites of warm-blooded animals contain as the active ingredient at least one of the said products to combat, for example, all sorts of ticks and gales.

When the compositions are to be used to combat animal parasitic acariens, the active compounds of formula I are very often incorporated into alimentary compositions in association with a nutritive mixture adapted to the animal to be fed. The nutritive mixture will vary depending upon the specific animal but usually contains cereals, sugars and grains, soybean, peanuts and turnsole press cake or meal of animal origin such as fish meal, synthetic amino acids, mineral salts, vitamins and antioxidants.

The compositions of the invention also have fungicidal properties and are useful against fungi such as Aerobacter aerogenes, Botrytis cinerea and Fusarium roseum. The compositions may also contain other active compounds and are preferably in the form of a powder for foliar spray containing 25 to 95% by weight of the compound of formula I or powder for foliar powdering containing 2.5 to 99% by weight of the compound of formula I.

To increase the pesticidal activity of the compositions of the invention, classical synergists may be incorporated therein such as 1-(2,5,8-trioxadodecyl)-2-propyl-4,5-methylenedioxy-benzene (piperonyl butoxide) or N-(2-ethylheptyl)-bicyclo-[2,2-1]-5-heptene-2,3-dicarboximide or piperonyl-bis-2-(2'-n-butoxy-ethoxy)-ethyl acetal (tropital).

Another feature of the invention are insecticidal, fungicidal, acaricidal or nematocidal compositions containing as an active ingredient at least one compound of formula I and as a second active ingredient at least one pyrethrinoid ester selected from the group consisting of esters of allethrolone, of 3,4,5,6-tetrahydrophthalimido-methyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclo-propane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropyl-acetic acids, esters of allethrolones, 3,4,5,6-tetrahydrophthalimido-methyl alcohol, 5-benzyl-3-furyl-methyl alcohol, 3-phenoxybenzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of formula I are in all possible stereoisomer forms, the same as the acid and alcohol moieties of the pyrethrinoid esters or their analogues above.

The latter associated compositions of the invention are of particular interest for combatting by the polyvalence of their action a larger range of parasites or by manifesting a synergistic action in some cases.

The novel method of the invention for combatting parasites such as insects, nematodes and acariens comprises contacting the parasites with a pesticidally effective amount of at least one compound of formula I.

In the following examples there are described several preferred embodiments to illustrate the invention. However, it is to be understood that the invention is not intended to be limited to the specific embodiments.

EXAMPLE 1

(S) cyano-(4-fluoro-3-phenoxy-phenyl)-methyl 2,2,3,3-tetramethyl-cyclopropane-1-carboxylate 1 ml of pyridine was added to a mixture of 1.27 g of 2,2,3,3-tetramethyl-cyclopropane-1-carboxylic acid chloride, 15 ml of benzene and 1.5 g of (R,S) cyano-(4-fluoro-3-phenoxy-benzyl)-methanol and the mixture was stirred for 18 hours at 20° C. Water was added thereto followed by 3 ml of 2N hydrochloric acid and the mixture was extracted with ethyl acetate. The organic phase was washed with water, dried and evaporated to dryness under reduced pressure. The residue was chromatographed over silica gel and eluted with a 9-1 hexane-ethyl acetate mixture to obtain 1.78 g of product. The latter was crystallized from hexane to obtain 1.46 g of (S) cyano-(4-fluoro-3-phenoxy-phenyl)-methyl 2,2,3,3-tetramethyl-cyclopropane-1-carboxylate melting at 100° C. and having a specific rotation of $[\alpha]_D^{20} = +4.5°$ (c=0.5% in chloroform).

EXAMPLE 2

(S) cyano-(4-fluoro-3-phenoxy-phenyl)-methyl (1R,trans) 2,2-dimethyl-3-[1(R,S), 2-dibromo-2,2-dichloroethyl]-cyclopropane-1-carboxylate 1 ml of pyridine was added to a mixture of 3.15 g of (1R,trans) 2,2-dimethyl-3-[1(R,S), 2-dibromo-2,2-dichloroethyl]-cyclopropane-1-carboxylic acid chloride, 25 ml of benzene and 1.51 g of (R,S) cyano-(4-fluoro-3-phenoxy-phenyl)-methanol and the mixture was stirred at 20° C. for 18 hours. Water was added to the mixture followed by addition of 8 ml of 2N hydrochloric acid and the mixture was extracted with benzene. The organic phase was washed with water, dried and evaporated to dryness under reduced pressure. The residue was chromatographed over silica gel and eluted with a 9-1 hexane-ethyl acetate mixture to obtain 2.56 g of (S) cyano-(4-fluoro-3-phenoxy-phenyl)-methyl (1R,trans) 2,2-dimethyl-3-(1(R,S) 2-dibromo-2,2-dichloroethyl)-cyclopropane-1-carboxylate with a specific rotation of $[\alpha]_D^{20} = +8°$ (c=0.8% in chloroform).

EXAMPLE 3

Using the procedure of Example 2, (R,S) cyano-(4-fluoro-3-phenoxy-benzyl)-methanol and (1R,cis) 2,2dimethyl-3-[1(R,S) 2-dibrom-2,2-dichloro-ethyl]-cycopropane-1-carboxylic acid chloride were reacted to obtain (S) cyano-(4-fluoro-3-phenoxy-phenyl)-methyl (1R,cis) 2,2-dimethyl-3-[1(R,S) 2-dibromo-2,2-dichlor-ethyl]-cyclopropane-1-carboxylate with a specific rotation of $[\alpha]_D^{20} = +16.5°$ (c=0.5% in chloroform).

EXAMPLE 4

Using the procedure of Example 2, (R,S) cyano-(4-fluoro-3-phenoxy-benzyl)-methanol and (1R,trans) 2,2-dimethyl-3-[1(R,S) 2,2,2-tetrabromoethyl]-cyclopropane-1-carboxylic acid chloride were reacted to obtain (S) cyano-(4-fluoro-3-phenoxy-phenyl)-methyl (1R,trans) 2,2-dimethyl-3-[1(R,S) 2,2,2-tetrabromoethyl]-cyclopropane-1-carboxylate with a specific rotation of $[\alpha]_D^{20} = +5°$ (c=0.7% in chloroform).

EXAMPLE 5

Using the procedure of Example 2, (R,S) cyano-(4-fluoro-3-phenoxy-phenyl)-methanol and (1R,cis) 2,2-dimethyl-3-[1(R,S) 2,2,2-tetrabromo-ethyl]-cyclopropane-1-carboxylic acid chloride were reacted to obtain (S) cyano-(4-fluoro-3-phenoxy-phenyl)-methyl (1R,cis) 2,2-dimethyl-3-[1,(R,S) 2,2,2-tetrabromoethyl]-cyclopropane-1-carboxylate with a specific rotation of $[\alpha]_D^{20} = +9°$ (c=0.5% in chloroform).

EXAMPLE 6

Using the procedure of Example 2, (R,S) cyano-(4-fluoro-3-phenoxy-phenyl)-methanol and (1R,trans) 2,2-dimethyl-3-[2,2-difluoroethenyl]cyclopropane-1-carboxylic acid chloride were reacted to obtain (S) cyano-(4-fluoro-3-phenoxy-phenyl)-methyl (1R,trans) 2,2-dimethyl-(3-[2,2-difluroethenyl]-cyclopropane-1-carboxylate with a specific rotation of $[\alpha]_D^{20} = -13°$ (c=1% in chloroform).

EXAMPLE 7

Using the procedure of Example 2, (R,S) cyano-(4-fluoro-3-phenoxy-phenyl)-methanol and (1R,cis) 2,2-dimethyl-3-[2,2-difluoroethenyl]-cyclopropane-1-carboxylic acid chloride were reacted to obtain (S) cyano-(4-fluoro-3-phenoxy-phenyl)-methyl (1R,cis) 2,2-dimethyl-3-[2,2-difluoroethenyl]-cyclopropane-1-carboxylate with a specific rotation of $[\alpha]_D^{20} = +24°$ (c=0.4% in chloroform).

EXAMPLE 8

(S) cyano-(4-fluoro-3-phenoxy-phenyl)-methyl (1R,trans) 2,2-dimethyl-3-cyclopentylidenemethyl-cyclopropane-1-carboxylate 10 ml of a methylene chloride solution containing 1.17 g of (1R,trans) 2,2-dimethyl-3-cyclopentylidene methylcyclopropane-1-carboxylic acid was poured with stirring over 5 minutes into a mixture of 1.25 ml of 1-dimethylamino-1-chloro-2-methyl-1-propene [described in J. Org. Chem., Vol. 35 (1970), p. 3970] and 10 ml of methylene chloride and the mixture was stirred for 20 minutes. A mixture of 1.44 g of (R,S) cyano-(4-fluoro-3-phenoxy-phenyl)-methanol, 1.25 ml of pyridine and 10 ml of methylene chloride was added to the mixture which was then stirred at room temperature for 3 hours. Water followed by 5 ml of 2N hydrochloric acid were added thereto and the decanted organic phase was washed with water, dried and evaporated to dryness under reduced pressure. The residue was chromatographed over silica gel and was eluted with a 9-1 hexane-ethyl acetate mixture to obtain 1.25 g of (S) cyano-(4-fluoro-3-phenoxy-phenyl)-methyl (1R,trans) 2,2-dimethyl-3-cyclopentylidenemethyl-cyclopropane-1-carboxylate with a specific rotation of $[\alpha]_D^{20} = -24.5°$ (c=0.5% in chloroform).

EXAMPLE 9

Using the procedure of Example 8, (R,S) cyano-(4-fluoro-3-phenoxy-phenyl)-methanol and (1R,cis) 2,2-dimethyl-3-cyclopentylidenemethyl-cyclopropane-1-carboxylic acid were reacted to obtain (S) cyano-(4-fluoro-3-phenoxy-phenyl)-methyl (1R,cis) 2,2-dimethyl-3-cyclopentylidenemethyl-cyclopropane-1-carboxylate with a specific rotation of $[\alpha]_D^{20} = +71.5°$ (c=0.5% in chloroform) and melting at 81° C.

EXAMPLE 10

Using the procedure of Example 8, (R,S) cyanio-(4-fluoro-3-phenoxy-phenyl)-methanol and (1R,trans) 2,2-dimethyl-3-[(dihydro-2-oxo-3-(2H)-thienylidene)-methyl]-cyclopropane-1-carboxylic acid were reacted to obtain (S) cyano-(4-fluoro-3-phenoxy-phenyl)-methyl (1R,trans) 2,2-dimethyl-3-[(dihydro-2-oxo-3-(2H)-thienylidene)-methyl]-cyclopropane-1-carboxylate with a specific rotation of $[\alpha]_D^{20} = -25°$ (c=0.75% in chloroform).

EXAMPLE 11

Using the procedure of Example 8, (R,S) cyano-(4-fluoro-3-phenoxy-phenyl)-methanol and (1R,cis) 2,2-dimethyl-3-[(dihydro-2-oxo-3-(2H)-thienylidene)-methyl]-cyclopropane-1-carboxylic acid were reacted to obtain (S) cyano-(4-fluoro-3-phenoxy-phenyl)-methyl (1R,cis) 2,2-dimethyl-3-[(dihydro-2-oxo-3-(2H)-thienylidene)-methyl]-cyclopropane-1-carboxylate with a specific rotation of $[\alpha]_D^{20} = +79°$ (c=0.5% in chloroform) and melting at 131° C.

EXAMPLE 12

Using the procedure of Example 8, (R,S) cyano-(4-fluoro-3-phenoxy-phenyl)-methanol and 2 (S)-[p-difluoromethoxyphenyl]-3-methyl-butyric acid were reacted to obtain (S) cyano (4-fluoro-3-phenoxy-phenyl)-methyl 2 (S)-[p-difluoromethoxy-phenyl]-3-methyl-butyrate with a specific rotation of $[\alpha]_D^{20} = +3.5°$ (c=0.6% in chloroform).

EXAMPLE 13

(S) cyano-(4-fluoro-3-phenoxy-phenyl)-methyl (1R,trans) 2,2-dimethyl-3-cyclobutylidene-methyl-cyclopropane-1-carboxylate STEP A: (1R,2R,5S) 6,6-dimethyl-3-oxa-2-[(R) cyano-(3-phenoxy-4-fluoro-phenyl)-methoxy]-bicyclo(3,1,0) hexane (product A) and (1R,2R,5S) 6,6-dimethyl-3-oxa-2-[(S) cyano-(3-phenoxy-4-fluoro-phenyl)-methoxy]-bicyclo (3,1,0) hexane (product B)

A mixture of 16 g of (R,S) cyano-(4-fluoro-3-phenoxy-phenyl)-methanol, 100 ml of dichloromethane, 9.4 g of (1R,2R,5S) 6,6-dimethyl-3-oxo-bicyclo (3,1,0)hexane-2-ol and 0.1 g of p-toluene sulfonic acid was relfuxed for 90 minutes and was poured into dilute aqueous potassium bicarbonate solution. The decanted organic phase was evaporated to dryness under reduced pressure to obtain 25.06 g of a mixture of products A and B. The mixture was chromatographed over silica gel and eluted with a 8-2 hexane-ether mixture to obtain first 8.85 g of (1R,2R,5S) 6,6-dimethyl-3-oxa-2-[(R) cyano-(3-phenoxy-4-fluoro-phenyl)-methoxy]-bicyclo (3,1,0)-hexane (product A) melting at <50° C. and having a specific rotation of $[\alpha]_D^{20} = +102°$ (c=1% in benzene) and then 9.05 g of (1R,2R,5S) 6,6-dimethyl-3-oxa-2-[(S) cyano-(3-phenoxy-4-fluoro-phenyl)-methoxy]-bicyclo (3,1,0) hexane (product B) melting at 65° C. and having a specific rotation of $[\alpha]_D^{20} = +50°$ (c=0.4% in benzene).

Circular Dichroism (dioxane):

| Product A | max. at 279 nm | $\Delta\epsilon = -0.27$ |
|---|---|---|
| Product B | Inflex. to 275 nm | $\Delta\epsilon = +0.13$ |
| | max. at 281 nm | $\Delta\epsilon = +0.15$ |

NMR Spectrum (deuterochloform):

Product A: Peaks at 1.07 ppm (hydrogens of geminal methyls); at 1.33–1.78 ppm (hydrogens of cyclopropyl); at 3.7–4.1 ppm (hydrogens of —CH2O); at 5.2–5.5 ppm (hydrogen of —OCH—); at 6.9–7.6 ppm (aromatic hydrogens).

Product B: Peaks at 1.0 ppm (hydrogens of geminal methyls); at 1.55–1.57 ppm (hydrogens) of cyclopropyl; at 3.8–3.9 ppm and 4.1–4.3 ppm (hydrogens of —CH2O); at 4.9–5.3 ppm (hydrogens of —OCH—); at 6.9–7.6 ppm (aromatic hydrogens).

STEP B: (S) cyano-(4-fluoro-3-phenoxy-phenyl)-methanol

A mixture of 9 g of product B from Step A, 100 ml of methanol and 90 mg of p-toluene sulfonic acid was stirred at 20° C. for 90 minutes and was then poured into water. The mixture was extracted with chloroform and the organic phase was evaporated to dryness under reduced pressure. The residue was chromatographed over silica gel and eluted with a 7-3 hexane-ethyl acetate mixture containing 1% of acetic acid to obtain 4.5 g of (S) cyano-(4-fluoro-3-phenoxy-phenyl)-methanol with a specific rotation of $[\alpha]_D^{20} = -30°$ (c=0.5% in pyridine).

STEP C: (S) cyano-(4-fluoro-3-phenoxyphenyl)-methyl (1R,trans) 2,2-dimethyl-3-cyclobutylidenemethyl-cyclopropane-1-carboxylate A mixture of 2 g of (1R,trans) 2,2-dimethyl-3-cyclobutylidene-methyl-cyclopropane-1-carboxylic acid, 2 g of dicyclohexylcarbodiimide, a small amount of 4-dimethylaminopyridine and 20 ml of methylene chloride was stirred at 20° C. for 15 minutes and then a solution of 1 g of the product of Step B in 5 ml of methylene chloride was progressively added thereto. The mixture was stirred at 20° C. for 17 hours and was filtered. The filtrate was evaporated to dryness under reduced pressure and the residue was chromatographed over silica gel. Elution with a 9-1 hexane-isopropyl ether mixture yielded 1.1 g of (S) cyano-(4-fluoro-3-phenoxy-phenyl)-methyl (1R,trans) 2,2-dimethyl-3-cyclobutylidenemethyl-cyclopropane-1-carboxylate.

Analysis: $C_{25}H_{24}FNO_3$; molecular weight=405.44

| Calculated: | % C 74.05 | % H 5.96 | % F 4.67 | % N 3.45 |
|---|---|---|---|---|
| Found: | 74.3 | 6 | 4.8 | 3.4 |

NMR Spectrum (deuterochloroform): Peaks at 1.14–1.18 ppm (hydrogens of geminal methyls); at 1.42–1.50 ppm (1-hydrogen of cyclopropyl; at 1.66 to 2.25 ppm (hydrogens of 3-methylene of cyclobutyl); at 2.5–2.9 ppm (hydrogens of 2- and 4-methylenes of cyclobutyl); at 4.8–4.9 ppm (ethylenic hydrogen); at 6.9–7.6 ppm (aromatic hydrogens).

EXAMPLE 14

(S) cyano-(4-fluoro-3-phenoxy-phenyl)-methyl (1R,cis) 2,2-dimethyl-3-cyclopropylidene-methyl-cyclopropane-1-carboxylate A solution of 1.04 g of (1R,cis) 2,2-dimethyl-3-cyclopropylidene-methyl-cyclopropane-1-carboxylic acid in 15 ml of methylene chloride was progressively added at 20° C. to a solution of 2.32 g of 1-chloro-N,N,2-trimethyl-propenylamine in 15 ml of methylene chloride and the mixture was stirred for one hour. A solution of 1.5 g of (S) cyano-(4-fluoro-3-phenoxy-phenyl)-methanol in 15 ml of methylene chloride and 1.2 ml of pyridine was progressively added to the mixture which was stirred at 20° C. for 16 hours. The mixture was poured into dilute aqueous hydrochloric acid solution and the decanted organic phase was evaporated to dryness under reduced pressure. The residue was chromatographed over silica gel and eluted with 9-1 hexane-ethyl acetate mixture to obtain 0.98 g of (S) cyano-(4-fluoro-3-phenoxy-phenyl)-methyl (1R,cis) 2,2-dimethyl-3-cyclopropylidene-methyl-cyclopropane-1-carboxylate melting at 101° C. and having a specific rotation of $[\alpha]_D^{20} = +76.5°$ (c=1% in chloroform).

EXAMPLE 15

(S) cyano-(3-phenoxy-4-fluoro-phenyl)-methyl (1R,trans) 2,2-dimethyl-3-cyclopropylidene-methyl-cyclopropane-1-carboxylate 1.33 g of dicyclohexylcarbodiimide were added with stirring to a mixture of 1.12 g of (1R,trans) 2,2-dimethyl-3-cyclopropylidene-methyl-cyclopropane-1-carboxylic acid, 0.2 ml of pyridine and 10 ml of methylene chloride and the mixture was stirred at 20° C. for 45 minutes. A solution of 1.9 g of (S) cyano-(4-fluoro-3-phenoxy-phenyl)-methanol in 10 ml of dichloromethane was progressively added to the mixture which was stirred for 24 hours at 20° C. and was poured into a dilute aqueous hydrochloric acid solution. The mixture was extracted with chloroform and the organic phase was evaporated to dryness under reduced pressure. The residue was chromatographed over silica gel and eluted with a 9-1 hexane-ethyl acetate mixture to obtain 1.56 g (S) cyano-(3-phenoxy-4-fluoro-phenyl)-methyl (1R,trans) 2,2-dimethyl-3-cyclopropylidene-methyl-cyclopropane-1-carboxylate with a specific rotation of $[\alpha]_D^{20} = -28°$ (c=0.7% in chloroform).

Analysis: $C_{24}H_{22}FNO_3$; molecular weight=351.446.

| Calculated: | % C 73.64 | % H 5.66 | % N 3.58 | % F 4.85 |
|---|---|---|---|---|
| Found: | 73.5 | 5.7 | 3.5 | 4.8 |

EXAMPLE 16

(S) cyano-(4-fluoro-3-phenoxy-phenyl)-methyl (1R,cis) 2,2-dimethyl-3-cyclobutylidenemethyl-cyclopropane-1-carboxylate A mixture of 1.1 g of dicyclohexylcarbodiimide, 0.2 ml of pyridine, 1 g of (1R,cis) 2,2-dimethyl-3-cyclobutylidene-methyl-cyclopropane-1-carboxylate and 20 ml of methylene chloride was stirred at 20° C. for 30 minutes and then a solution of 1 g of (S) cyano-(4-fluoro-3-phenoxy-phenyl)-methanol in 5 ml of methylene chloride was progressively added to the mixture which was stirred at 20° C. for 17 hours and was filtered. The filtrate was evaporated to dryness under reduced pressure and the residue was chromatographed over silica gel. Elution with a 9-1 cyclohexane-ethyl acetate mixture and then a 9-1 hexane-isopropyl ether mixture yielded 1.1 g of (S) cyano-(4-fluoro-3-phenoxy-phenyl)-methyl (1R,cis) 2,2-dimethyl-3-cyclobutylidenemethyl-cyclopropane-1-carboxylate.

Analysis: $C_{25}H_{24}FNO_3$; molecular weight=405.44.

| Calculated: | % C 74.05 | % H 5.46 | % F 4.69 | % N 3.45 |
|---|---|---|---|---|
| Found: | 73.9 | 6.0 | 4.8 | 3.5 |

NMR Spectrum (deuterochloroform): Peaks at 1.18–1.20 ppm (hydrogens of geminal methyls); at 2.6–2.9 ppm (hydrogens of 2- and 4-methylenes of cyclobutyl); at 5.2–5.4 ppm (ethylenic hydrogens); at 6.6 ppm (hydrogen on carbon attached to —CN); at 7.1–7.6 ppm (aromatic hydrogens).

EXAMPLE 17

A soluble concentrate or aqueous spray was prepared by homogeneously mixing 0.25 g of the product of Example 1, 1 g of piperonyl butoxide, 0.25 g of Tween 80, 0.1 g of Topanol A and 98.4 g of water.

An emulsifiable concentrate was prepared by intimately mixing 0.015 g of the product of Example 1, 0.5 g of piperonyl butoxide, 3.5 g of Tween 80, 0.1 g of Topanol A and 95.885 g of xylene.

An emulsifiable concentrate was prepared by homogeneously mixing 1.5 g of the product of Example 1, 20 g of Tween 80, 0.1 g of Topanol A and 78.4 g of xylene.

A fumigant composition was prepared containing 0.25 g of the product of Example 1, 25 g of Tabu powder, 40 g of cedar needle powder, 33.75 g of pinewood powder. 0.5 g of brilliant green and 0.5 g of p-nitrophenol.

PESTICIDAL ACTIVITY

A. Knockdown activity against houseflies

Female houseflies 4 days old were sprayed in a Kearns and March chamber at 2 ml per second with a solution of 5% of acetone and 95% of Isopar L with 50 insects being used for each dose at a concentration of 0.25 g/liter and readings were taken every 30 seconds for 10 minutes and after 15 minutes to determine the $KT_{50}$ by the usual method. The results are reported in Table I.

TABLE I

| Product of Example | $KT_{50}$ in minutes |
|---|---|
| 1 | 2.0 |
| 2 | 2.8 |
| 3 | 2.9 |
| 4 | 2.0 |
| 5 | 4.8 |
| 6 | 1.6 |
| 7 | 1.7 |
| 8 | 6.1 |
| 9 | 4.4 |
| 10 | 3.5 |
| 11 | 3.5 |
| 12 | 3.6 |
| 13 | 2.74 |
| 14 | 3.13 |
| 15 | 2.85 |
| 16 | 2.89 |

B. Lethal activity against houseflies 50 female houseflies 4 to 5 days old per treatment received a topical application of 1 μl of an acetone solution of the test compound on the dorsal thorax with an Arnold micromanipulator and the number of dead flies was determined 24 hours later. The $DL_{50}$ or dose in nanograms per fly necessary to kill 50% of the insects were determined and the results are reported in Table II.

TABLE II

| Product of Example | $DL_{50}$ namograms per insects |
|---|---|
| 1 | 5.3 |
| 2 | 1.14 |
| 3 | 1.02 |
| 4 | 1.04 |
| 5 | 0.58 |
| 6 | 8.9 |
| 7 | 1.9 |
| 8 | 0.98 |
| 9 | 0.87 |
| 11 | 21.3 |
| 12 | 4.9 |
| 13 | 0.97 |
| 14 | 1.44 |
| 15 | 2.04 |

TABLE II-continued

| Product of Example | $DL_{50}$ namograms per insects |
|---|---|
| 16 | 0.639 |

C. Lethal activity against beetles

The tests were effected by contact with a film on glass deposited by pipette of acetone solutions of different concentrations on the bottom of a glass Petrie dish with sides previously coated with talc to avoid loss of insects. The $CL_{50}$ or dose which killed 50% of the insects was determined and the results are reported in Table III.

TABLE III

| Compound of Example | $CL_{50}$ in $mg/m^2$ |
|---|---|
| 1 | 0.22 |
| 2 | 0.084 |
| 3 | 0.021 |
| 4 | 0.074 |
| 5 | 0.037 |
| 6 | 0.126 |
| 7 | 0.029 |
| 8 | 0.054 |
| 9 | 0.083 |
| 12 | 0.23 |
| 13 | 0.029 |
| 14 | 0.049 |
| 15 | 0.137 |
| 16 | 0.018 |

D. Lethal effect against Spodoptera Larvae

1 μl of acetone solution of the test compound was applied with an Arnold micromanipulator to the dorsal thorax of 15 larvae of Spodoptera littoralis in the 4th stage of development which are about 10 days old at 24° C. and 65% relative humidity. After treatment, the larvae were placed on an artificial nutritive media and the number of dead was determined 48 hours later. The results are reported in Table IV.

TABLE IV

| Compound of Example | $DL_{50}$ ng per insect |
|---|---|
| 1 | 8.4 |
| 2 | 6.2 |
| 3 | 1.4 |
| 4 | 6.5 |
| 5 | 1.6 |
| 6 | 3.4 |
| 7 | 2.2 |
| 8 | 14.9 |
| 9 | 5.1 |
| 11 | 8.2 |
| 12 | 44.3 |
| 13 | 5.8 |
| 14 | 4.25 |
| 15 | 4.6 |
| 16 | 4.5 |

E. Lethal activity against Acanthocelides obtectus

Test D was repeated on larvae of Acanthocelides obtectus to determined the $DL_{50}$ thereof and the results are reported in Table V.

TABLE V

| Compound of Example | $DL_{50}$ in ng per insect |
|---|---|
| 1 | 8.12 |

TABLE V-continued

| Compound of Example | DL₅₀ in ng per insect |
|---|---|
| 2 | 10.9 |
| 3 | 7.7 |
| 4 | 6.7 |
| 5 | 16.1 |
| 6 | 7.1 |
| 7 | 7.4 |
| 8 | 20.1 |
| 9 | 8.6 |
| 11 | 50.6 |
| 12 | 22.2 |
| 13 | 17.9 |
| 14 | 22.7 |
| 15 | 31.2 |
| 16 | 12.3 |

From Tables I to V, it can be seen that the compounds of Examples 1 to 16 have a good insecticidal activity.

F. Acaricidal activity

Bean plants with 2 leaves were infested with 25 female Tetranychus urticae per leaf and were placed in an airy place with a lighted ceiling with constant light. The plants were treated with a Fischer pistol with 4 ml of a toxic solution at 50 ppm per plant in a 1-1 mixture of water and acetone. The plants were dried for 12 hours and were then infested. The number of dead was determined 72 hours later and the dosage rate was 5 g per hectoliter. The compounds of Examples 1 to 16 all showed a good acaricidal activity.

G. Nematocidal activity

About 2000 nematodes of Panagrellus silusae suspended in 0.5 ml of water were placed in a 50 ml receptacle and then 10 ml of an aqueous solution containing 1 or 0.1 g/l were added thereto. 3 tests were run for each concentration and after 24 hours, the aqueous mixture was homogenized and samples of 1 ml were taken and the number of living and dead nematodes were counted using a Peter plate and the results were expressed as a ratio with respect to untreated controls. The compounds of Examples 1 to 16 all showed a good nematocidal activity in this test.

H. Fungicidal activity = Activity against Botrytis Cinerea

Zones of inhibition obtained from wheat seeds treated with a gelose nutritive media enriched with a suspension of spores of test mushrooms were used to evalutate the test compounds. A suspension of spores of Botrytis cinerea in carrot juice was incorporated into a culture medium constituted of potato, dextrose and agar and was adjusted to 50,000 spores per gram of media. Seeds of champlain wheat were treated with a quanity of test compound corresponding to 80 g of active material per 100 Kilograms of seeds and the treated seeds were placed in the contaminated culture media. 4 bottles containing 5 grains were used for each dose and after 6 days of incubation at 20° C., the zones of inhibition were measured. The results were expressed as a percentage of efficiency as compared to a parallel test with untreated controls and the compounds of Example 1 to 16 all showed a good activity in this test.

I. Activity against Fusarium roseum

The development of a mushroom issuing from spores in a gelose nutritive media with the test compound was studied. 5 ml of a suspension of the test compound in sterile water was added to 45 ml of the gelose nutritive media (acidified malt). The concentrations used were 100, 10 and 1 ppm of active compound. The mixture was divided under sterile conditions into 2 Petrie bottles and after solidification, 4 cellulose pastilles enriched with a drop of Spore suspension of 200,000 spores of Fusarium roseum per ml of sterile water were placed at 4 points in the Petri bottle. Readings were effected 7 days later by measuring the eight colonies in the 2 bottles and the average diameter of the colonies served as the criteria as compared to the untreated controls. The average percent of efficacy was determined and the compounds of Examples 1 to 16 showed a good activity in this test.

Activity against Rhizoctonia solani

The efficacy of the test compounds was determined in a bed of treated grains with the soil artifically contaminated with one volume of a culture Rhizoctonia solani bran and vermiculite enriched with Knopp liquid per 29 volumes of a mixture of ⅓ of pure dirt, ⅓ of sand and ⅓ of Polish peat. The grains were Beta vulgaris (monogerm beets) and were treated with the test compounds at a rate of 240 g per 100 Kilograms and the contaminated soil was divided into 5 pots containing 20 treated grains each. After 12 days of storage at 20° C., the number of sound plants was determined and the results were expressed as a percentage of efficacy as compared to untreated controls. The compounds of Examples 1 to 16 all showed a good activity in this test.

Various modifications of the products and processes of the invention may be made without departing from the spirit or scope thereof and it should be understood that the invention is intended to be limited only as defined in the appended claims.

What we claim is:

1. A compound selected from the group consisting of esters in their steriosomeric form or mixtures thereof of the formula

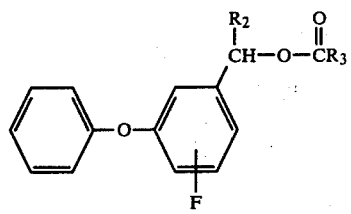

wherein $R_2$ is selected from the group consisting of —CN and —C≡CH and $R_3$ is

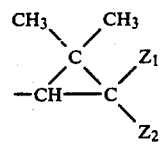

$Z_1$ is hydrogen and $Z_2$ is selected from the group consisting of

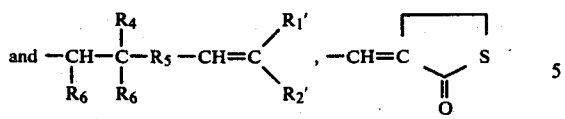

$R_1'$ and $R_2'$ taken together with the carbon atom to which they are attached form cycloalkylidene of 3 to 6 carbon atoms $R_4$, $R_5$ and $R_6$ are individually halogen.

2. A compound of claim 1 wherein $R_2$ is —CN.

3. A compound of claim 1 wherein $R_1$ is in the 4-position.

4. A compound of claim 1 or 3 wherein $R_3$ is

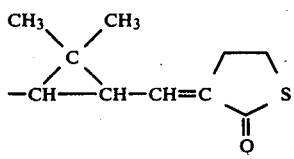

5. A compound of claim 1 or 3 wherein $R_3$ is

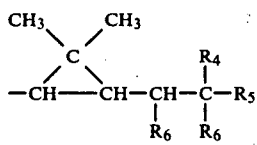

6. A compound of claim 1 or 5 wherein $R_3$ is

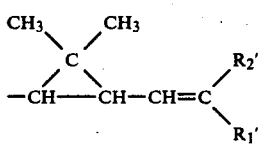

wherein

form a cycloalkylidene of 3 to 6 carbon atoms.

7. An insecticidal composition comprising an insecticidally effective amount of at least one compound of claim 1 and an inert carrier.

8. A composition of claim 7 wherein $R_2$ is —CN.

9. A composition of claim 7 wherein $R_1$ is in the 4-position.

10. A composition of claim 7 wherein $R_3$ is

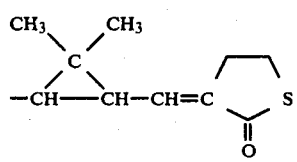

11. A composition of claim 7 wherein $R_3$ is

12. A composition of claim 7 wherein $R_3$ is

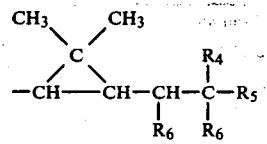

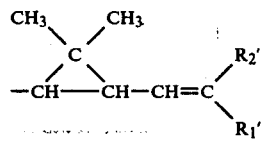

wherein

form a cycloalkylidene of 3 to 6 carbon atoms.

13. A method for combatting pests of vegetables, of warm-blooded animals and of permises comprising contacting them with a pesticidally effective amount of at least one compound of claim 1 and an inert carrier.

14. A method of combatting insects comprising contacting insects with an insecticidally effective amount of at least one compound of claim 1.

15. A method of claim 4 wherein in the compound $R_2$ is —CN.

16. A method of claim 14 wherein in the compound $R_1$ is in the 4-position.

17. A method of claim 14 wherein in the compound $R_3$ is

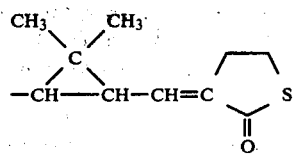

18. A method of claim 14 wherein in the compound $R_3$ is

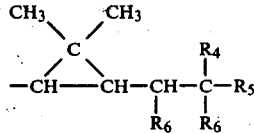

19. A method of claim 14 wherein $R_3$ is

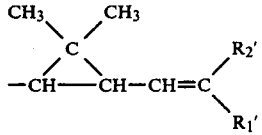

wherein

form a cycloalkylidene of 3 to 6 carbon atoms.

20. A method of combatting nematodes comprising contacting nematodes with a nematocidally effective amount of at least one compound of claim 1.

21. A method of combatting acariens comprising contacting acariens with an acaricidally effective amount of at least one compound of claim 1.

22. A method of claim 21 wherein in the compound $R_2$ is —CN.

23. A method of claim 21 wherein in the compound $R_1$ is in the 4-position.

24. A method of claim 21 wherein in the compound $R_3$ is

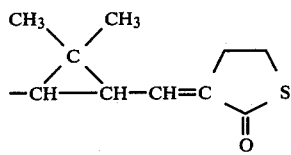

25. The method of claim 21 wherein in the compound $R_3$ is

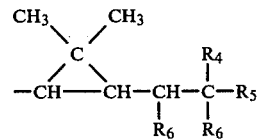

26. A method of claim 21 wherein in the compound $R_3$ is

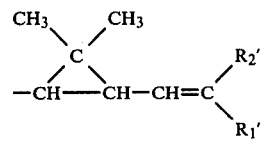

wherein

form a cycloalkylidene of 3 to 6 carbon atoms.

27. A method of combatting affections caused by acariens in warm-blooded animals comprising contacting warm-blooded animals with an anti-acarienly effective amount of at least one compound of claim 1.

28. A method of combatting fungus comprising contacting fungus with a fungicidally effective amount of at least one compound of claim 1.

* * * * *